US012685504B2

(12) United States Patent
Nishijima et al.

(10) Patent No.: US 12,685,504 B2
(45) Date of Patent: Jul. 21, 2026

(54) RADIATION IMAGING SYSTEM

(71) Applicant: CANON KABUSHIKI KAISHA, Tokyo (JP)

(72) Inventors: Katsuhiro Nishijima, Kanagawa (JP); Daisuke Yamada, Kanagawa (JP); Kazuma Obara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 370 days.

(21) Appl. No.: 18/493,542

(22) Filed: Oct. 24, 2023

(65) Prior Publication Data

US 2024/0138801 A1     May 2, 2024

(30) Foreign Application Priority Data

Oct. 27, 2022  (JP) ................................. 2022-172095
Oct. 27, 2022  (JP) ................................. 2022-172096
Oct. 27, 2022  (JP) ................................. 2022-172097

(51) Int. Cl.
*A61B 6/00*       (2024.01)
*A61B 6/40*       (2024.01)

(52) U.S. Cl.
CPC .............. *A61B 6/542* (2013.01); *A61B 6/405* (2013.01)

(58) Field of Classification Search
CPC ....... A61B 6/4233; A61B 6/405; A61B 6/542; A61B 6/469; A61B 6/465; A61B 6/5205; A61B 6/5211; A61B 6/4291; A61B 6/585; A61B 6/463; A61B 6/467; A61B 6/545; A61B 6/48; A61B 6/50; A61B 6/52; A61B 6/06; A61B 6/544; A61B 6/56; A61B 6/032; A61B 6/461; A61B 6/502; A61B 6/4464; A61B 6/54; A61B 5/7221; A61B 6/4283; A61B 6/548; A61B 6/58; A61B 6/4441; A61B 6/482; A61B 6/504; A61B 6/5217; A61B 6/5294; A61B 6/42; A61B 6/4208; A61B 6/4241; A61B 6/4266; A61B 6/547; A61B 2560/0276; H04N 23/30; G06N 3/08; G16H 30/40; G16H 50/20;

(Continued)

(56) References Cited

U.S. PATENT DOCUMENTS

2013/0251106 A1*  9/2013  Tajima ................. A61B 6/4233
                                                                   378/97
2014/0177798 A1*  6/2014  Kitagawa ................. A61B 6/56
                                                                   378/62

(Continued)

FOREIGN PATENT DOCUMENTS

JP        2021090665 A      6/2021
JP        2021108910 A      8/2021

(Continued)

*Primary Examiner* — Irakli Kiknadze
(74) *Attorney, Agent, or Firm* — Canon U.S.A., Inc. IP Division

(57)        ABSTRACT

A radiation imaging system includes a radiation imaging apparatus configured to transmit, based on electric charge generated in response to irradiation with radiation and a target value, a signal related to control of irradiation with radiation to an external apparatus; and a control apparatus configured to generate a target dose index value that is based on the target value and a dose index value that is based on information regarding electric charge, and determine whether the dose index value is within an allowable range of the target dose index value.

22 Claims, 15 Drawing Sheets

(58) Field of Classification Search
CPC . G16H 50/30; G06T 7/11; G06T 2207/20084;
G06T 2207/10116; G06T 2207/20081;
G06T 2207/30004; G06T 2207/20104;
G06T 7/0012; G06T 2207/30068; G01T
1/02; G01T 1/17; G01T 1/161; G01T
1/08; G01N 23/04; G21K 5/10; G01V
5/22
USPC ...................................................... 378/98, 62
See application file for complete search history.

(56)                     References Cited

U.S. PATENT DOCUMENTS

2014/0205066 A1* 7/2014 Kitagawa ............... H04N 23/30
378/62
2015/0182182 A1* 7/2015 Tajima ................... A61B 6/542
378/189
2016/0183908 A1* 6/2016 Hayashida ........... A61B 6/4291
378/207
2017/0172535 A1* 6/2017 Kim ....................... A61B 6/502
2018/0333128 A1   11/2018 Obara
2022/0313199 A1   10/2022 Nishii

FOREIGN PATENT DOCUMENTS

JP          2021191391 A    12/2021
JP          2022158892 A    10/2022

\* cited by examiner

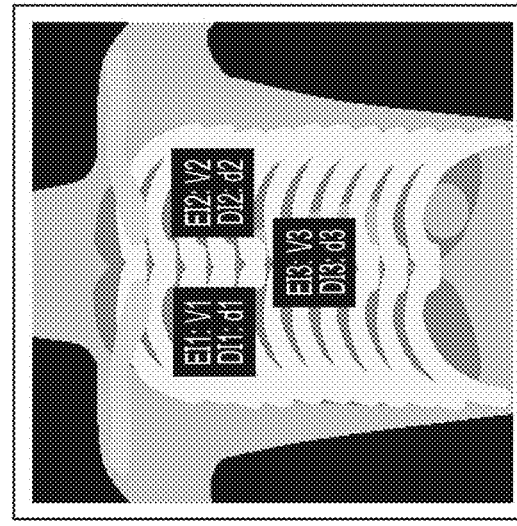
FIG. 8B
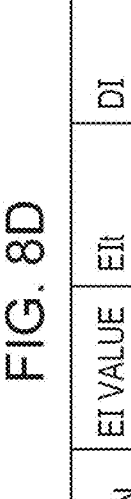
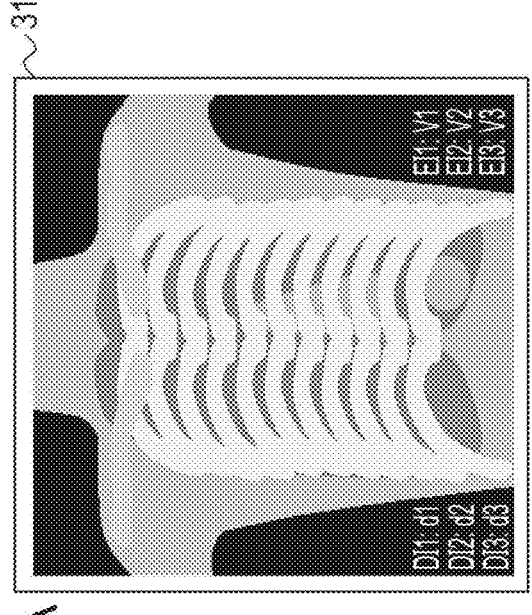
FIG. 8A
314
FIG. 8C
314
FIG. 8D
| IMAGE REGION | EI VALUE | EIt | DI |
|---|---|---|---|
| 1 | V1 | T1 | d1 |
| 2 | V2 | T2 | d2 |
| 3 | V3 | T3 | d3 |
| 4 | V4 | T4 | d4 |
| 5 | V5 | T5 | d5 |

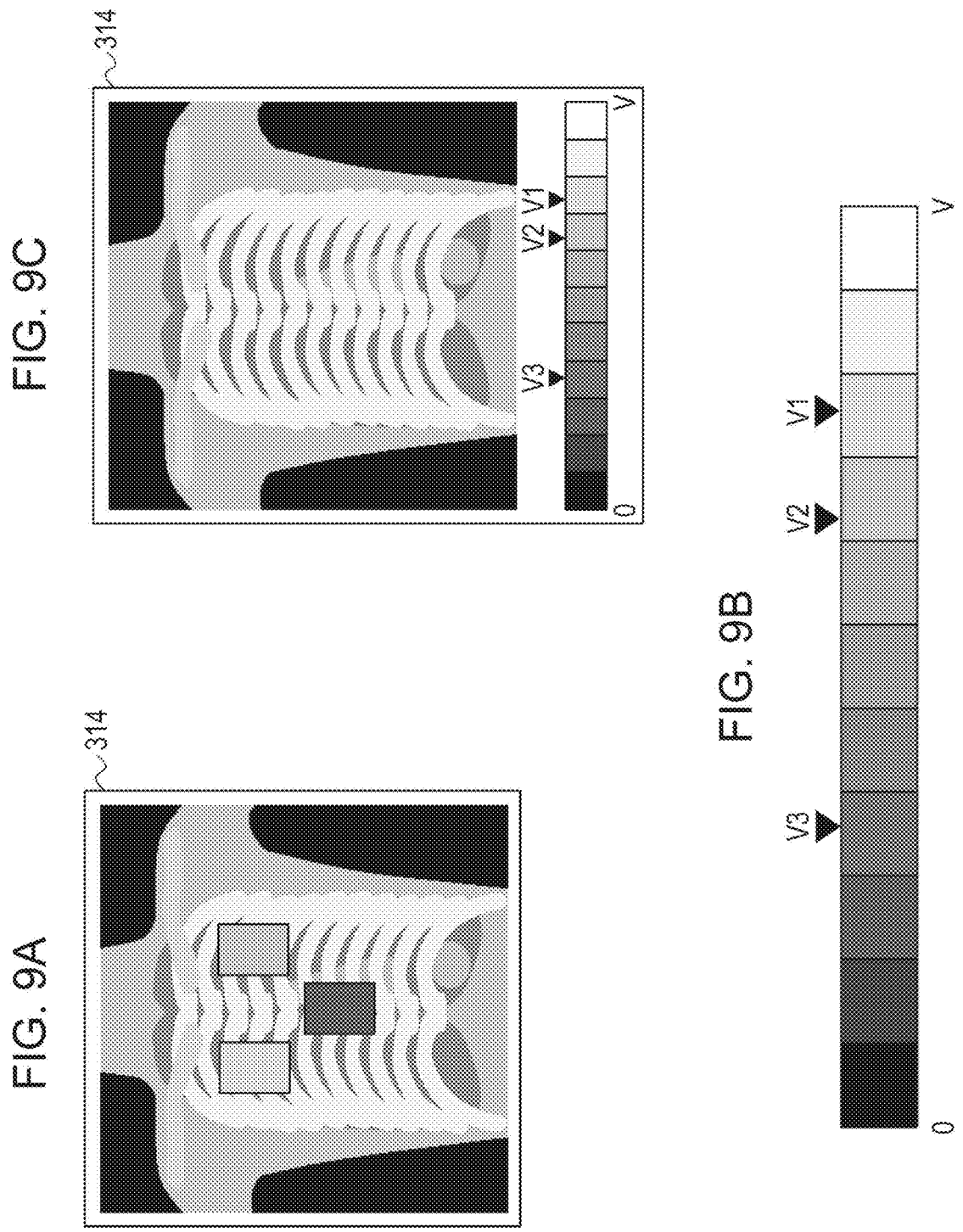

| IMAGE REGION | EI VALUE |
|---|---|
| A | 100 |
| B | 110 |
| C | 120 |

| STOP CONDITION | SPECIFIED EI VALUE |
|---|---|
| AND | 100 |
| OR | 120 |
| AVG | 110 |

FIG. 12

| IMAGE REGION | EI VALUE |
|---|---|
| A | 100 |
| B | 110 |
| C | 120 |

(a) AND — 110 100 120

(b) OR — 110 100 120

(c) AVG — 110 100 120

(d) AND — 80 70 90

FIG. 13

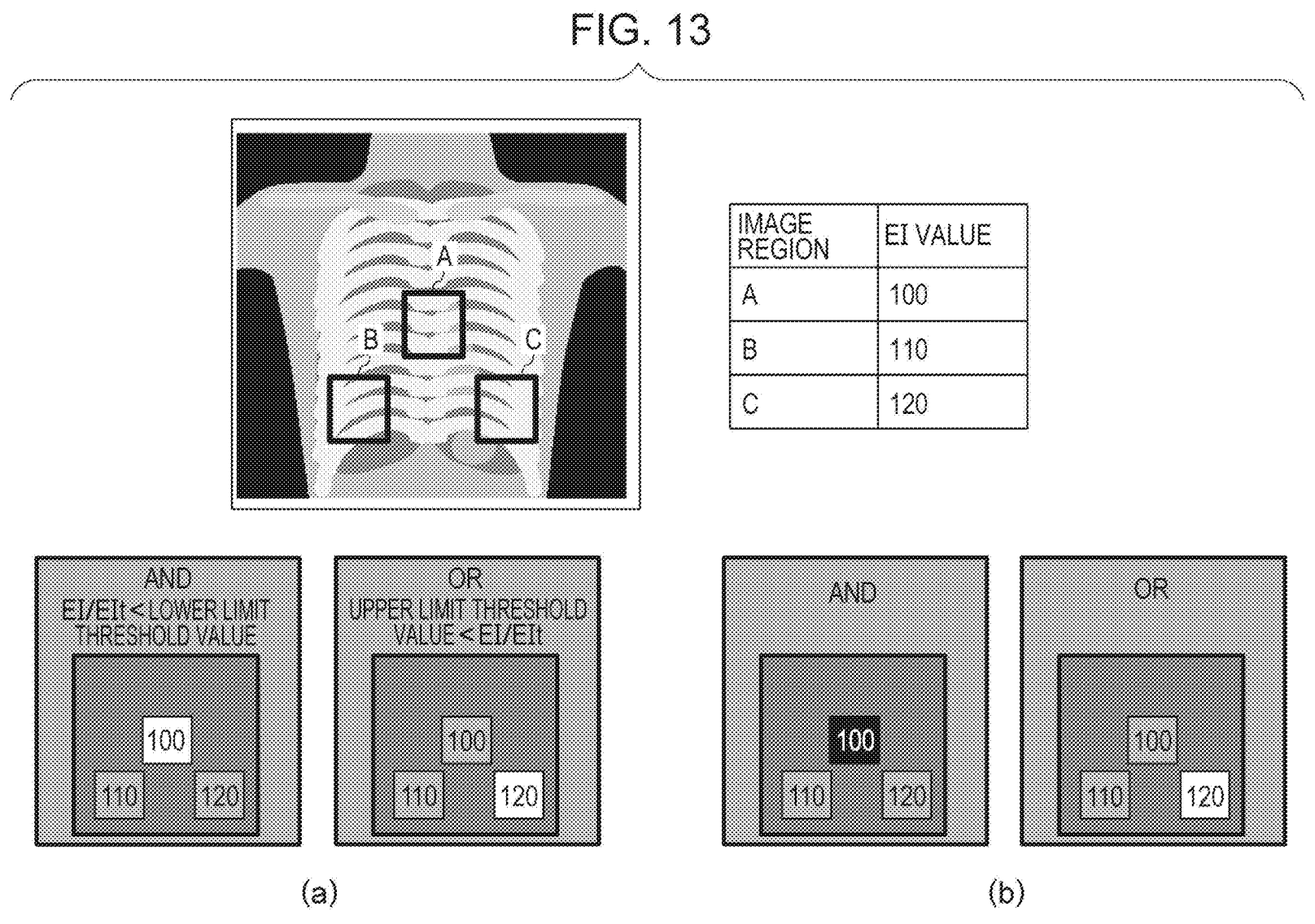

| IMAGE REGION | EI VALUE |
|---|---|
| A | 100 |
| B | 110 |
| C | 120 |

(a)

AND
EI/EIt<LOWER LIMIT THRESHOLD VALUE

OR
UPPER LIMIT THRESHOLD VALUE<EI/EIt (b)

AND

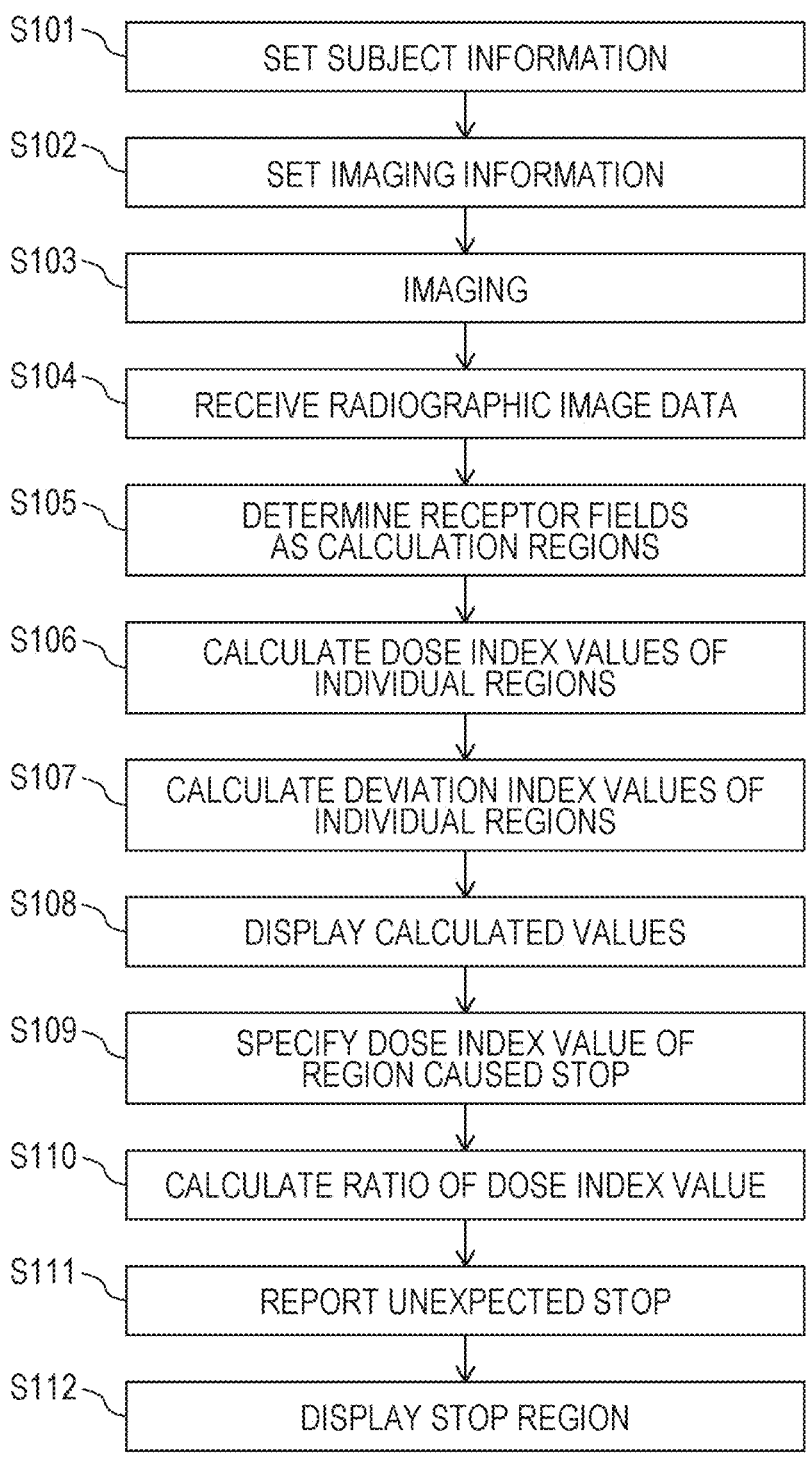

S101 — SET SUBJECT INFORMATION

S102 — SET IMAGING INFORMATION

S103 — IMAGING

S104 — RECEIVE RADIOGRAPHIC IMAGE DATA

S105 — DETERMINE RECEPTOR FIELDS AS CALCULATION REGIONS

S106 — CALCULATE DOSE INDEX VALUES OF INDIVIDUAL REGIONS

S107 — CALCULATE DEVIATION INDEX VALUES OF INDIVIDUAL REGIONS

S108 — DISPLAY CALCULATED VALUES

S109 — SPECIFY DOSE INDEX VALUE OF REGION CAUSED STOP

S110 — CALCULATE RATIO OF DOSE INDEX VALUE

S111 — REPORT UNEXPECTED STOP

S112 — DISPLAY STOP REGION

~314

D1 d1
D2 d2

EI1 V1
EI2 V2

R2
R1  R3  R5
R4

| IMAGE REGION | REACHED DOSE MONITORING FUNCTION | EI VALUE | EIt | DI |
|---|---|---|---|---|
| R1 | ON | V1 | T1 | d1 |
| R2 | ON | V2 | T2 | d2 |
| R3 | OFF | V3 | T3 | d3 |
| R4 | OFF | V4 | T4 | d4 |
| R5 | OFF | V5 | T5 | d5 |

RADIATION IMAGING SYSTEM

This application claims the benefit of Japanese Patent Application No. 2022-172096, filed on Oct. 27, 2022, Japanese Patent Application No. 2022-172097, filed on Oct. 27, 2022, and Japanese Patent Application No. 2022-172095, filed Oct. 27, 2022, which are hereby incorporated by reference herein in their entirety.

BACKGROUND OF THE INVENTION

Field of the Invention

The present invention relates to a radiation imaging apparatus and a radiation imaging system.

Description of the Related Art

As a radiation imaging apparatus used for medical image diagnosis or nondestructive inspection using radiation such as X-rays, a radiation imaging apparatus including a matrix substrate having a pixel array in which a switch such as a thin film transistor (TFT) and a conversion element such as a photoelectric conversion element are combined has been put into practical use.

In recent years, multifunctionality of a radiation imaging apparatus has been studied. For example, incorporation of a function of monitoring irradiation with radiation has been studied. This function enables, for example, detection of a timing at which radiation starts being emitted from a radiation source, detection of a timing at which irradiation with radiation is to be stopped, and detection of the amount of irradiation or the integrated amount of irradiation with radiation.

Japanese Patent Laid-Open No. 2021-191391 discloses that a radiation imaging apparatus and a radiation control apparatus perform wireless communication to transmit signals related to exposure control, and that the radiation imaging apparatus instructs the radiation control apparatus to stop irradiation with radiation. If an irradiation stop signal indicating that irradiation with radiation has stopped is not received from the radiation control apparatus until a first time elapses after a stop instruction signal is transmitted, the radiation imaging apparatus transmits a stop instruction signal to the radiation control apparatus again. Accordingly, there is provided a technique advantageous in suppressing a decrease in the accuracy of exposure control due to a communication failure.

The use of automatic exposure control (AEC) makes it possible to capture a radiographic image with an optimum dose.

However, the technique disclosed in Japanese Patent Laid-Open No. 2021-191391 is susceptible to improvement in determining or confirming whether AEC is operating correctly. In view of these issues, the present invention relates to a technique of determining whether AEC is operating correctly.

SUMMARY OF THE INVENTION

A first radiation imaging system according to an embodiment of the present invention includes a radiation imaging apparatus and a control apparatus. The radiation imaging apparatus includes a conversion unit configured to generate electric charge in response to irradiation with radiation; and a transmission unit configured to transmit, based on the electric charge generated by the conversion unit and a target value, a signal related to control of irradiation with radiation to an external apparatus. The control apparatus includes a dose index generating unit configured to generate a target dose index value that is based on the target value, and a dose index value that is based on information regarding electric charge, the information being acquired from the radiation imaging apparatus; an allowable range setting unit configured to set an allowable range of the target dose index value; and a determination unit configured to determine whether the dose index value is within the allowable range.

A second radiation imaging system according to an embodiment of the present invention includes a radiation imaging apparatus and a control apparatus. The radiation imaging apparatus includes a conversion unit configured to generate electric charge in response to irradiation with radiation; and a transmission unit configured to transmit, based on the electric charge generated by the conversion unit and a target value, a signal related to control of irradiation with radiation to an external apparatus. The control apparatus includes a dose index generating unit configured to generate a target dose index value that is based on the target value, and a dose index value that is based on information regarding electric charge, the information being acquired from the radiation imaging apparatus; an allowable range setting unit configured to set an allowable range of the target dose index value; and a determination unit configured to determine whether the dose index value is within the allowable range. The conversion unit includes a plurality of regions. The signal transmitted by the transmission unit is a signal for providing an instruction to stop irradiation with radiation, the signal being transmitted based on electric charge of each of the plurality of regions, the target value, and a stop condition. The dose index generating unit is configured to generate a dose index value for each of the plurality of regions of the conversion unit. The determination unit is configured to, in a case where the stop condition is AND, determine whether a smallest dose index value among the dose index values of the plurality of regions is within the allowable range.

A third radiation imaging system according to an embodiment of the present invention includes a radiation imaging apparatus and a control apparatus. The radiation imaging apparatus includes a conversion unit configured to generate electric charge in response to irradiation with radiation; and a transmission unit configured to transmit, based on the electric charge generated by the conversion unit and a target value, a signal related to control of irradiation with radiation to an external apparatus. The control apparatus includes a dose index generating unit configured to generate a target dose index value that is based on the target value, and a dose index value that is based on information regarding electric charge, the information being acquired from the radiation imaging apparatus; an allowable range setting unit configured to set an allowable range of the target dose index value; and a determination unit configured to determine whether the dose index value is within the allowable range. The conversion unit includes a plurality of regions. The signal transmitted by the transmission unit is a signal for providing an instruction to stop irradiation with radiation, the signal being transmitted based on electric charge of each of the plurality of regions, the target value, and a stop condition. The dose index generating unit is configured to generate a dose index value for each of the plurality of regions of the conversion unit. The determination unit is configured to, in a case where the stop condition is OR, determine whether a largest dose index value among the dose index values of the plurality of regions is within the allowable range.

A fourth radiation imaging system according to an embodiment of the present invention includes a radiation imaging apparatus and a control apparatus. The radiation imaging apparatus includes a conversion unit configured to generate electric charge in response to irradiation with radiation; and a transmission unit configured to transmit, based on the electric charge generated by the conversion unit and a target value, a signal related to control of irradiation with radiation to an external apparatus. The control apparatus includes a dose index generating unit configured to generate a target dose index value that is based on the target value, and a dose index value that is based on information regarding electric charge, the information being acquired from the radiation imaging apparatus; an allowable range setting unit configured to set an allowable range of the target dose index value; and a determination unit configured to determine whether the dose index value is within the allowable range. The conversion unit includes a plurality of regions. The signal transmitted by the transmission unit is a signal for providing an instruction to stop irradiation with radiation, the signal being transmitted based on electric charge of each of the plurality of regions, the target value, and a stop condition. The dose index generating unit is configured to generate a dose index value for each of the plurality of regions of the conversion unit. The determination unit is configured to, in a case where the stop condition is AVG, determine whether an average value of the dose index values of the plurality of regions is within the allowable range.

A fifth radiation imaging system according to an embodiment of the present invention includes a radiation imaging apparatus and a control apparatus. The radiation imaging apparatus includes a conversion unit configured to generate electric charge in response to irradiation with radiation; and a transmission unit configured to transmit, based on the electric charge generated by the conversion unit and a target value, a signal related to control of irradiation with radiation to an external apparatus. The control apparatus includes a dose index generating unit configured to generate a target dose index value that is based on the target value, and a dose index value that is based on information regarding electric charge, the information being acquired from the radiation imaging apparatus; an allowable range setting unit configured to set an allowable range of the target dose index value; a determination unit configured to determine whether the dose index value is within the allowable range; and a display unit configured to display a determination result. The conversion unit includes a plurality of regions. The signal transmitted by the transmission unit is a signal for providing an instruction to stop irradiation with radiation, the signal being transmitted based on electric charge of each of the plurality of regions, the target value, and a stop condition. The dose index generating unit is configured to generate a dose index value for each of the plurality of regions of the conversion unit. The determination unit is configured to, based on the stop condition, select at least one region among the plurality of regions and make a determination of whether the dose index value of the selected region is within the allowable range. The display unit is configured to, in a case where a determination result of the determination indicates that the dose index value of the selected region is out of the allowable range, display the determination result such that a position of the selected region is recognizable.

Further features of the present invention will become apparent from the following description of exemplary embodiments with reference to the attached drawings.

BRIEF DESCRIPTION OF THE DRAWINGS

FIG. 2 is a diagram illustrating a radiation imaging apparatus.

FIG. 6 is a diagram illustrating a control apparatus in the radiation imaging system.

FIGS. 8A to 8D are diagrams illustrating an example of a method for displaying dose index values.

FIGS. 9A to 9C are diagrams illustrating an example of a method for displaying dose index values.

FIG. 12 is a diagram illustrating an example of a method for displaying a stop region.

FIG. 13 is a diagram illustrating an example of a method for displaying a ratio outside a threshold of a stop region.

FIG. 14 is a diagram illustrating an example operation of the radiation imaging system.

DESCRIPTION OF THE EMBODIMENTS

Embodiment

Figure 1:
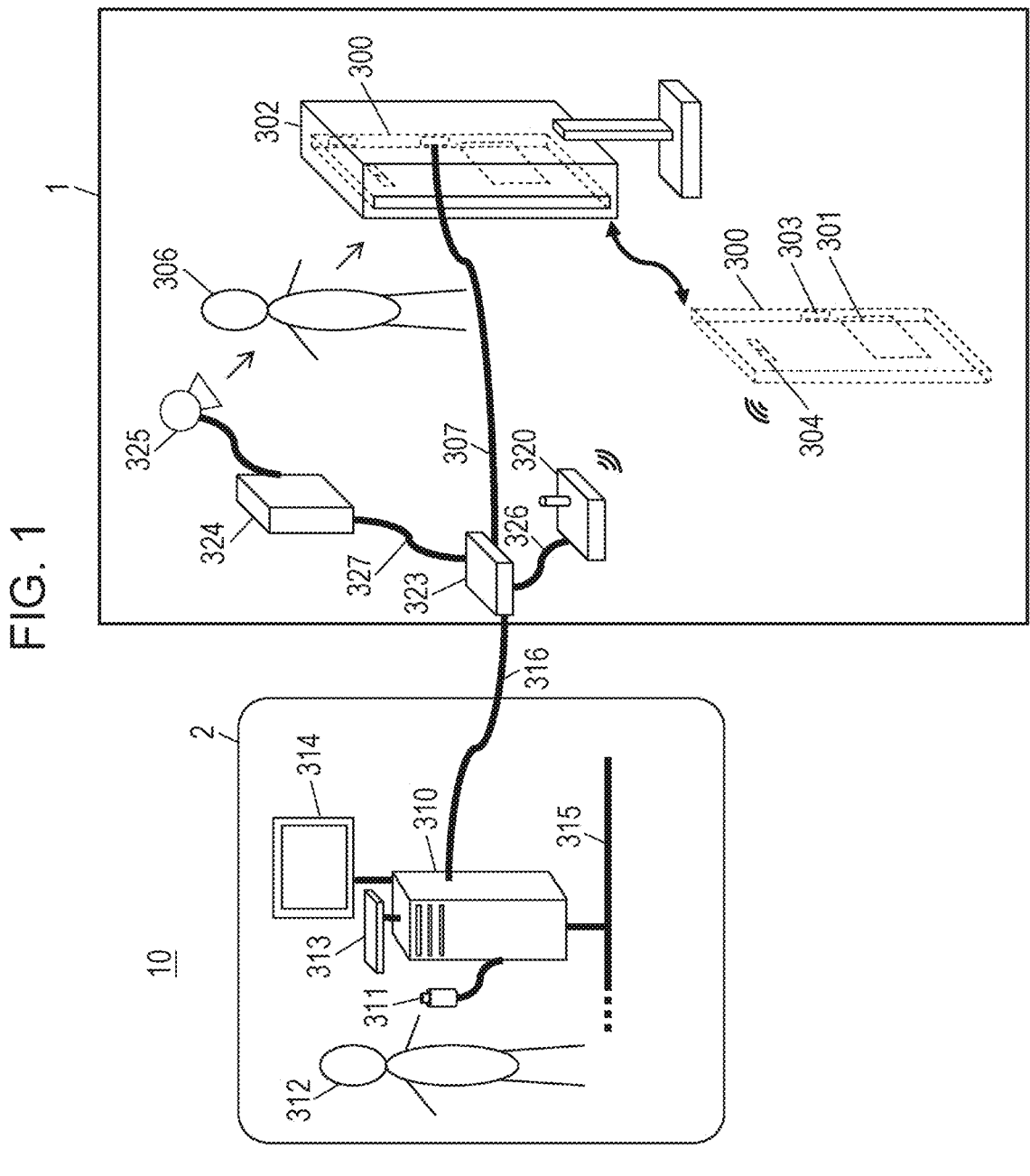
FIG. 1 is a diagram illustrating a radiation imaging system.

A radiation imaging system according to an embodiment will be described below with reference to the drawings. FIG. 1 is a diagram illustrating a radiation imaging system according to an embodiment.

As illustrated in FIG. 1, a radiation imaging system 10 is provided in a radiation room 1 for performing radiation imaging using radiation irradiation, and a control room 2 located near the radiation room 1.

The radiation room 1 is equipped with, as the radiation imaging system 10, a radiation imaging apparatus 300, an upright stand 302, a radiation-imaging-apparatus communication cable 307, an access point (AP) 320, and a communication control apparatus 323. Furthermore, the radiation room 1 is equipped with a radiation generating apparatus 324, a radiation source 325, an AP communication cable 326, and a radiation-generating-apparatus communication cable 327.

The control room 2 is equipped with, as the radiation imaging system 10, a control apparatus 310, a radiation irradiation switch 311, an input apparatus 313, a display apparatus 314, an in-hospital local area network (LAN) 315, and a radiation-room communication cable 316.

The radiation imaging apparatus 300 includes a power supply control unit 301 constituted by a battery or the like, a wired communication unit 303, and a wireless communication unit 304. The radiation imaging apparatus 300 detects radiation transmitted through a subject 306 and generates radiographic image data.

The wired communication unit 303 enables transmission and reception of information by cable connection using, for example, a communication standard having a predetermined agreement or a standard such as Ethernet.

The wireless communication unit 304 includes, for example, an antenna and a circuit board including a communication integrated circuit (IC) or the like. The circuit board including a communication IC or the like performs communication processing of a protocol based on a wireless LAN via the antenna. There is no particular limitation on the frequency band, standard, or method of wireless communication. A short-range wireless method such as near field communication (NFC) or Bluetooth, an ultra wide band (UWB), or the like may be used. The wireless communication unit 304 may have a plurality of wireless communication methods, and may perform communication by selecting a method from among the methods as appropriate. Hereinafter, the wired communication unit 303 and the wireless communication unit 304 may be collectively referred to as a communication unit, a transmission unit, or a reception unit, and the wired communication unit 303 and the wireless communication unit 304 may be individually referred to as a communication unit, a transmission unit, or a reception unit.

The upright stand 302 is a stand on which the radiation imaging apparatus 300 can be mounted to capture a radiographic image in an upright position. The radiation imaging apparatus 300 is attachable to and detachable from the upright stand 302, and is capable of performing imaging in both a state in which the radiation imaging apparatus 300 is attached thereto and a state in which the radiation imaging apparatus 300 is detached therefrom.

The radiation-imaging-apparatus communication cable 307 is a cable for connecting the radiation imaging apparatus 300 and the communication control apparatus 323.

The access point 320 performs wireless communication with the radiation imaging apparatus 300. For example, the access point 320 is used to relay communication between the radiation imaging apparatus 300 and the control apparatus 310 and communication between the radiation imaging apparatus 300 and the radiation generating apparatus 324 when the radiation imaging apparatus 300 is used while being detached from the upright stand 302. Although FIG. 1 illustrates an example in which communication is performed via the access point 320, either the radiation imaging apparatus 300 or the communication control apparatus 323 may serve as an access point to perform direct communication without using the access point 320.

The communication control apparatus 323 performs control so that the access point 320, the radiation generating apparatus 324, and the control apparatus 310 are capable of communicating with each other.

The radiation generating apparatus 324 controls the radiation source 325 to emit radiation based on a predetermined irradiation condition.

The radiation source 325 irradiates the subject 306 with radiation in accordance with the control of the radiation generating apparatus 324.

The AP communication cable 326 is a cable for connecting the access point 320 and the communication control apparatus 323.

The radiation-generating-apparatus communication cable 327 is a cable for connecting the radiation generating apparatus 324 and the communication control apparatus 323.

The control apparatus 310 communicates with the radiation generating apparatus 324 and the radiation imaging apparatus 300 via the communication control apparatus 323, and controls the radiation imaging system 10 in a centralized manner.

The radiation irradiation switch 311 inputs a timing of radiation irradiation in response to an operation performed by an operator 312.

The input apparatus 313 is an apparatus that inputs an instruction from the operator 312, and may be an input apparatus of various types, such as a keyboard or a touch panel.

The display apparatus 314 is an apparatus that displays radiographic image data subjected to image processing and a graphical user interface (GUI), and may be a display or the like.

The in-hospital LAN 315 is a backbone network in a hospital.

The radiation-room communication cable 316 is a cable for connecting the control apparatus 310 and the communication control apparatus 323 in the radiation room 1.

Figure 2:
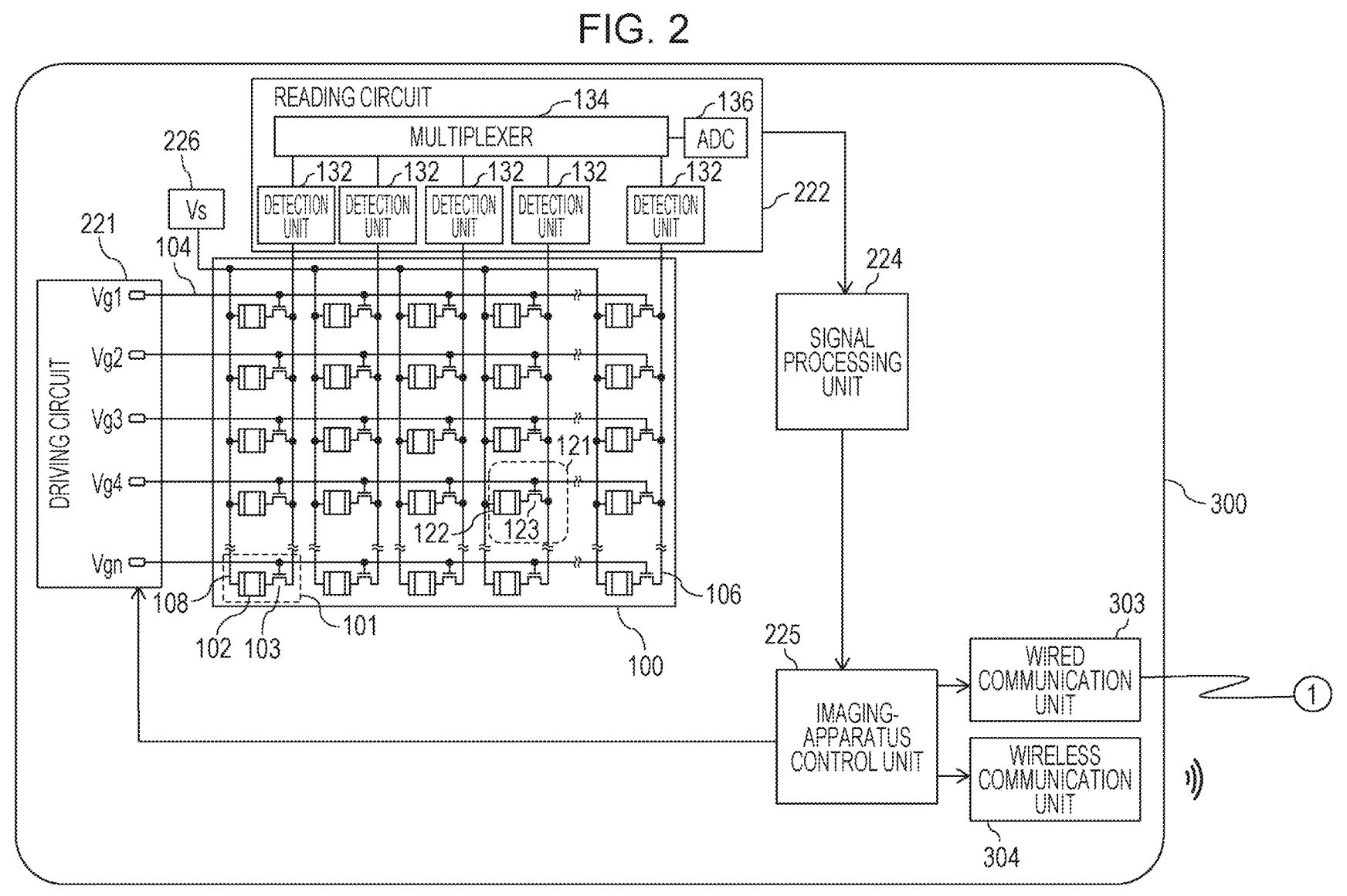

FIG. 2 is a diagram illustrating the radiation imaging apparatus 300. As illustrated in FIG. 2, the radiation imaging apparatus 300 includes a radiation detector 100. The radiation detector 100 has a function of detecting radiation used for irradiation. Specifically, the radiation detector 100 functions as a conversion unit that generates electric charge in response to irradiation with radiation. The radiation detector 100 (hereinafter also referred to as a conversion unit) includes a plurality of pixels arranged in a plurality of rows and a plurality of columns. In the following description, a region in which the plurality of pixels are arranged in the radiation detector 100 is referred to as a detection region. The plurality of pixels include an imaging pixel 101 and a correction pixel 121. The imaging pixel 101 is an imaging pixel for acquiring a radiographic image or radiation irradiation information (in the present invention, the imaging pixel will be hereinafter referred to as a detection pixel in order to describe the purpose of acquiring radiation irradiation information). The correction pixel 121 is a correcting pixel for removing a dark current component or a crosstalk component.

The detection pixel 101 may be used only for the purpose of acquiring a radiographic image or only for the purpose of acquiring radiation irradiation information. Furthermore, the detection pixel 101 may be used for the selected one of the purpose of acquiring a radiographic image and the purpose of acquiring radiation irradiation information, or may be used for both the purpose of acquiring a radiographic image and the purpose of acquiring radiation irradiation information.

The detection pixel 101 includes a first conversion element 102 that converts radiation into an electric signal, and a first switch 103 disposed between a column signal line 106 and the first conversion element 102.

The first conversion element 102 is constituted by a scintillator that converts radiation into light and a photoelectric conversion element that converts light into an electric signal. In the present embodiment, generating of electric charge in response to irradiation with radiation includes converting of radiation into light and converting of the light into an electric signal. The scintillator is typically formed in a sheet shape so as to cover the detection region, and is shared by a plurality of pixels. Alternatively, the first conversion element 102 is constituted by a conversion element that converts radiation directly into light.

The first switch 103 includes, for example, a thin film transistor (TFT) in which an active region is formed of a semiconductor such as amorphous silicon or polycrystalline silicon (polycrystalline silicon in one embodiment).

Figure 3:
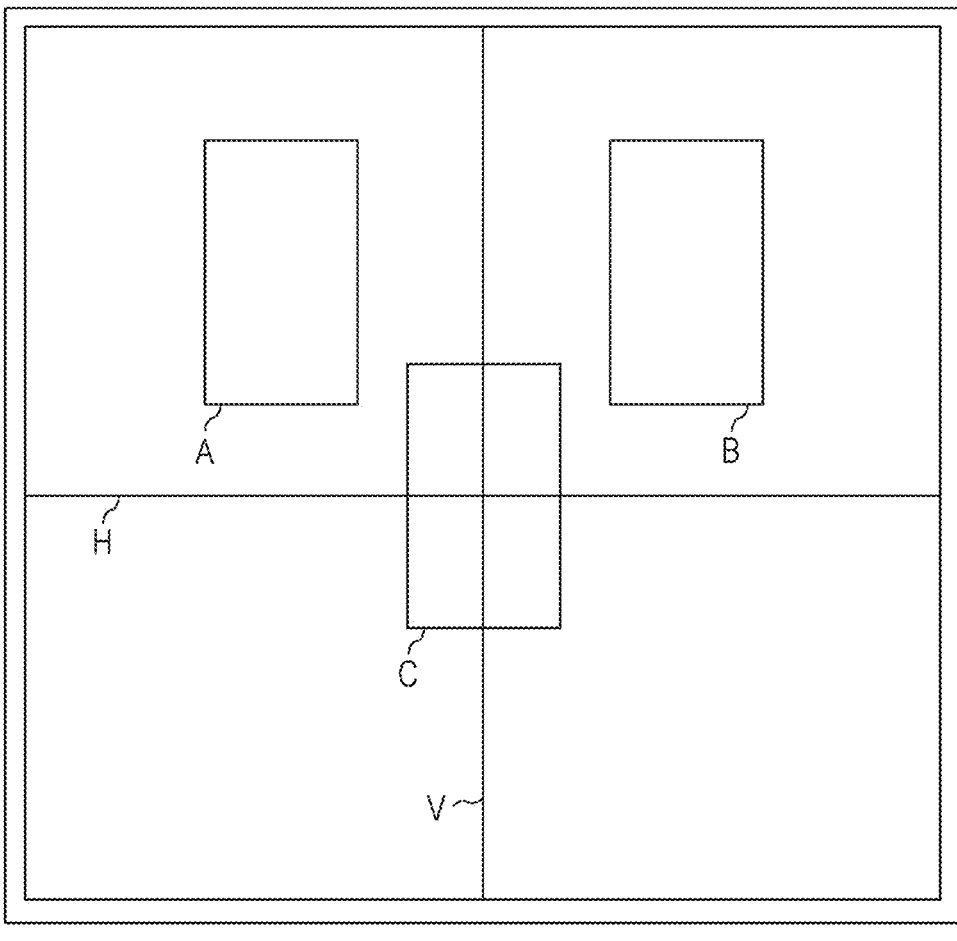
FIG. 3 is a diagram illustrating an example of arrangement of receptor fields and an imaging region.
Figure 4:
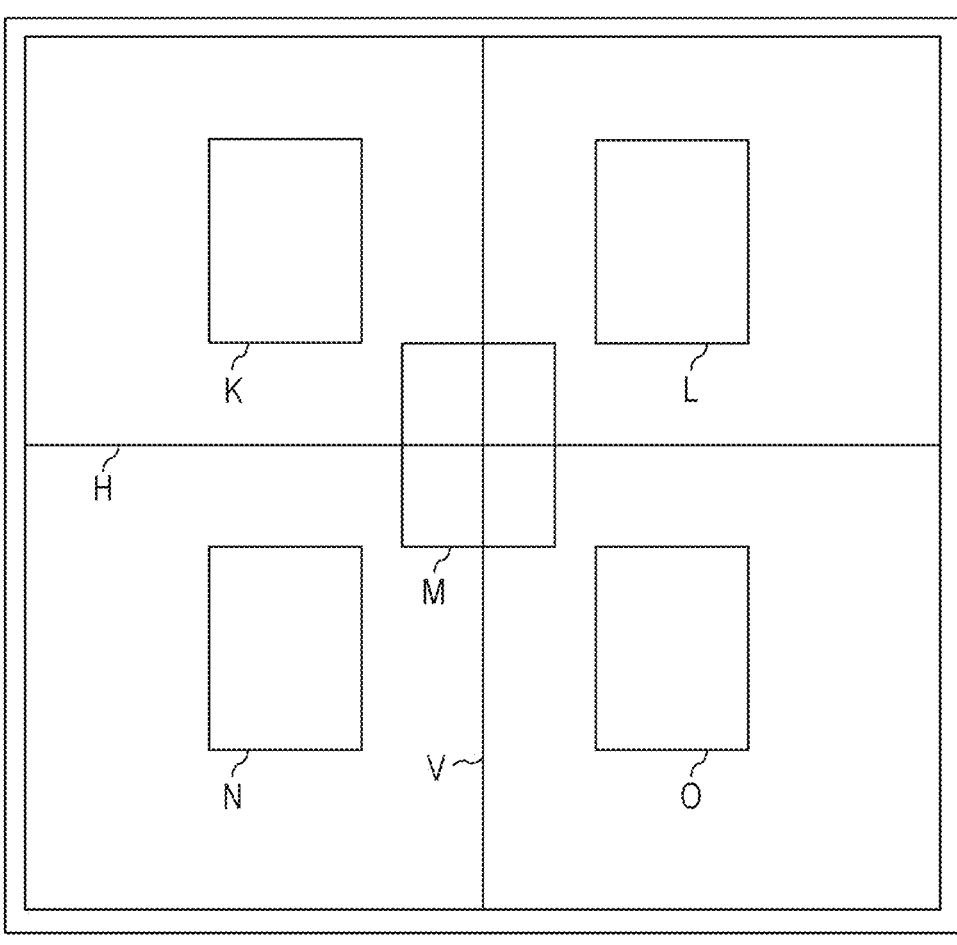
FIG. 4 is a diagram illustrating an example of arrangement of receptor fields and an imaging region.

The area in which the detection pixel 101 for acquiring radiation irradiation information and the correction pixel 121 are arranged is located at a certain position in the detection region of the radiation imaging apparatus 300. The area may be located, for example, in a plurality of regions, such as regions A to C in FIG. 3 or regions K to O in FIG. 4, similarly to an existing separate AEC sensor.

The radiation imaging apparatus 300 includes a plurality of column signal lines 106 and a plurality of drive lines 104.

Each column signal line 106 corresponds to one of a plurality of columns in the detection region. Each drive line 104 corresponds to one of a plurality of rows in the detection region.

Each drive line 104 is driven by a driving circuit 221.

The first conversion element 102 includes a first electrode connected to a first main electrode of the first switch 103, and a second conversion element 122 includes a first electrode connected to a first main electrode of a second switch 123. The first conversion element 102 and the second conversion element 122 each include a second electrode connected to a bias line 108. One bias line 108 extends in the column direction and is connected in common to the second electrodes of the plurality of conversion elements 102 and 122 arranged in the column direction.

The bias line 108 receives a bias voltage Vs from an element power supply circuit 226. The bias voltage Vs is supplied from the element power supply circuit 226.

The first switches 103 of a plurality of detection pixels 101 and the second switches 123 of a plurality of correction pixels 121 in one column include respective second main electrodes that are connected to one of the plurality of column signal lines 106. The first switches 103 of a plurality of detection pixels 101 and the second switches 123 of a plurality of correction pixels 121 in one row include respective control electrodes that are connected to one of the plurality of drive lines 104. The plurality of column signal lines 106 are connected to a reading circuit 222. The reading circuit 222 includes a plurality of detection units 132, a multiplexer 134, and an analog-to-digital converter (hereinafter an AD converter) 136.

Each of the plurality of column signal lines 106 is connected to a corresponding one of the plurality of detection units 132 of the reading circuit 222. Here, one column signal line 106 corresponds to one detection unit 132.

The detection unit 132 includes, for example, a differential amplifier. The multiplexer 134 selects the plurality of detection units 132 in a predetermined order and supplies signals from the selected detection units 132 to the AD converter 136.

The AD converter 136 converts the signals supplied thereto into digital signals and outputs the digital signals.

A signal processing unit 224 outputs, based on an output of the reading circuit 222 (the AD converter 136), information indicating irradiation of the radiation imaging apparatus 300 with radiation. Specifically, the signal processing unit 224 performs, for example, characteristic correction processing of removing a dark current component or a crosstalk component of the radiation imaging apparatus 300 using the correcting pixels, detection of irradiation with radiation, calculation of the amount of irradiation and the integrated amount of irradiation with radiation, and so forth.

An imaging-apparatus control unit 225 controls the driving circuit 221, the reading circuit 222, and so forth in accordance with information from the signal processing unit 224 or a control command from the control apparatus 310.

Figure 5:
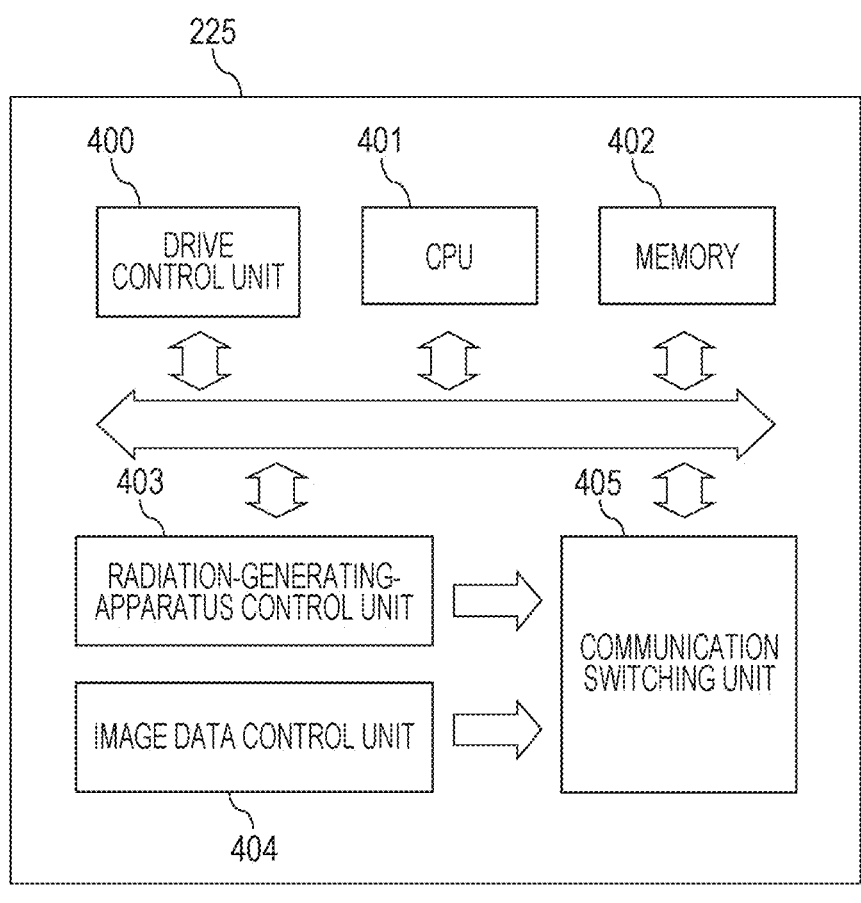
FIG. 5 is a diagram illustrating an imaging-apparatus control unit in the radiation imaging apparatus.

FIG. 5 is a diagram illustrating the imaging-apparatus control unit 225 of the radiation imaging apparatus 300. As illustrated in FIG. 5, the imaging-apparatus control unit 225 includes a drive control unit 400, a central processing unit (CPU) 401, a memory 402, a radiation-generating-apparatus control unit 403, an image data control unit 404, and a communication switching unit 405.

The drive control unit 400 controls the driving circuit 221 and the reading circuit 222 in accordance with information from the signal processing unit 224 or a command from the control apparatus 310.

The CPU 401 controls the entire radiation imaging apparatus 300 by using a program and various data stored in the memory 402.

The memory 402 stores, for example, a program and various data that are to be used by the CPU 401 to execute processing. The various data include various data obtained through processing performed by the CPU 401, and radiographic image data.

The radiation-generating-apparatus control unit 403 controls communication with the radiation generating apparatus 324 in accordance with information from the signal processing unit 224 or information from the drive control unit 400.

The radiation-generating-apparatus control unit 403 and the radiation generating apparatus 324 transmit and receive information regarding control of the radiation generating apparatus 324 (for example, a notification of the start of irradiation with radiation or the stop of irradiation with radiation, the amount of irradiation with radiation, the integrated amount of irradiation with radiation, or the like).

In response to a radiation dose in a radiation detection region (receptor field) for monitoring radiation reaching a reference threshold value which is a target value, the radiation-generating-apparatus control unit 403 provides, to the radiation generating apparatus 324, a stop notification which is information regarding the control of the radiation generating apparatus 324. The radiation-generating-apparatus control unit 403 may provide the stop notification to the control apparatus 310 instead of the radiation generating apparatus 324. In a case where the stop notification is provided to the control apparatus 310, the stop notification is provided to the radiation generating apparatus 324 from the control apparatus 310, and radiation irradiation is stopped. The radiation-generating-apparatus control unit 403 may provide the stop notification to the radiation generating apparatus 324 and may notify the control apparatus 310 of only whether the stop notification has been provided. In this way, the stop notification is provided from the radiation imaging apparatus 300 to an external apparatus in any one of these various notification patterns. The notification is not limited to a stop notification, and various notifications related to control of radiation irradiation, such as the start of irradiation, the amount of irradiation, and the integrated amount of irradiation, can be provided as described above. The receptor field corresponds to, for example, regions A to C in FIG. 3 and regions K to O in FIG. 4. With such a plurality of receptor fields being provided, the radiation detector 100 serving as a conversion unit includes a plurality of regions. As a result of such a plurality of receptor fields being set, information regarding radiation can be acquired for each receptor field.

The radiation-generating-apparatus control unit 403 provides a stop notification in response to the radiation dose in the receptor field selected as a target to be monitored reaching a reference threshold value which is a target value (hereinafter referred to as a reached dose monitoring function). In a case where a plurality of receptor fields are selected as a target to be monitored, for example, a stop notification may be provided in response to the radiation dose in any one of the selected receptor fields reaching the reference threshold value. In this case, the stop condition is an OR condition, which will be described in detail below. Alternatively, a stop notification may be provided in response to the radiation doses in all the selected receptor fields reaching the reference threshold value. In this case, the stop condition is an AND condition. The mode in which the radiation-generating-apparatus control unit 403 provides a stop notification is set by, for example, any one of the radiation imaging apparatus 300, the radiation generating apparatus 324, and the control apparatus 310. The mode in which radiation irradiation is not stopped in accordance with the reached radiation dose may be provided. There may be provided a system in which a general exposure control sensor (ion chamber/photo timer or the like), which is not illustrated, is attached to the outside of the radiation imaging apparatus 300 and radiation irradiation is stopped in accordance with the radiation dose. In the present embodiment, the radiation-generating-apparatus control unit 403 is provided. Alternatively, radiation irradiation may be detected by the signal processing unit 224 to perform radiation imaging without communication with the radiation generating apparatus 324.

The image data control unit 404 stores the image data from the reading circuit 222 in the memory 402, and controls communication with the control apparatus 310. The image data control unit 404 and the control apparatus 310 transmit and receive radiographic image data and information regarding control (for example, control commands or the like).

The communication switching unit 405 enables communication by the wired communication unit 303 in response to the radiation-imaging-apparatus communication cable 307 being connected to the radiation imaging apparatus 300. The communication switching unit 405 switches the communication unit so as to enable communication by the wireless communication unit 304 in response to the radiation-imaging-apparatus communication cable 307 being disconnected from the radiation imaging apparatus 300.

Figure 6:
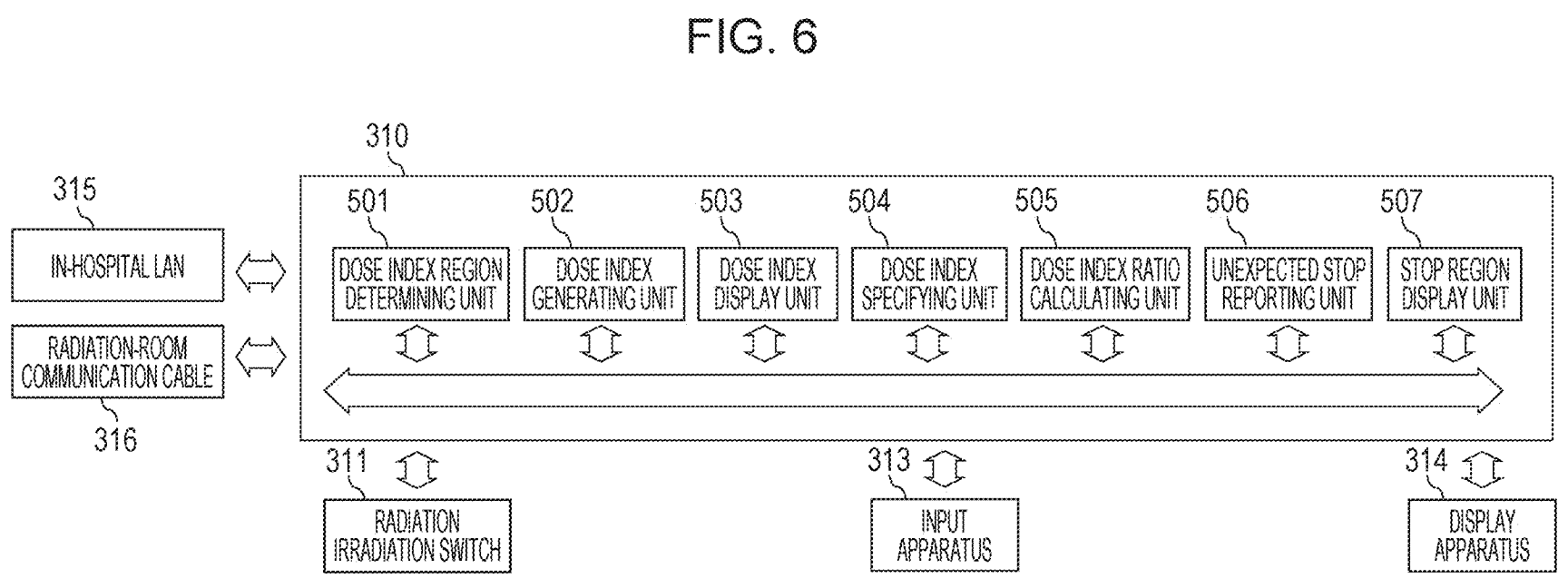

FIG. 6 is a diagram illustrating the control apparatus 310. As illustrated in FIG. 6, the control apparatus 310 includes a dose index region determining unit 501, a dose index generating unit 502, a dose index display unit 503, a dose index specifying unit 504, a dose index ratio calculating unit 505, an unexpected stop reporting unit 506, and a stop region display unit 507. The dose index ratio calculating unit 505 has a function of setting an allowable range of a target dose index value, which will be described below, and thus may be referred to as an allowable range setting unit in the following description. The dose index ratio calculating unit 505 also has a function of determining whether a dose index value is within a set allowable range, and thus may be referred to as a determination unit.

The dose index region determining unit 501 determines a region for which a dose index value is to be calculated in a radiographic image generated by the radiation imaging apparatus 300. The number of regions may be one, or two or more. In the present embodiment, the region is rectangle, but the shape is not limited thereto. The dose index value is, for example, an exposure index (EI) value. In the present embodiment, an EI value is used as a dose index value, but a similar technique is applicable to any other dose index values.

The dose index generating unit 502 calculates a dose index value of the region determined by the dose index region determining unit 501. A target dose index (for example, a target exposure index (EIt)) that can be determined as an optimum dose may be set for each region, and a deviation index (for example, DI) may be calculated. Specifically, for example, a dose index value is generated based on radiographic image information obtained from an electric signal generated by the conversion element 102. A target dose index value may be generated based on a target value (reference threshold value) of the radiation dose used for determination of an instruction to transmit a radiation stop signal by the radiation-generating-apparatus control unit 403.

The dose index display unit 503 displays the dose index value, the target dose index, and the deviation index generated by the dose index generating unit 502. The number of contents to be displayed may be one, or two or more. The display method may be changed in accordance with imaging conditions. In the present embodiment, the dose index region determining unit 501 and the dose index generating unit 502 are included in the control apparatus 310. Alternatively, these units may be included in the radiation imaging apparatus 300.

Figure 7:
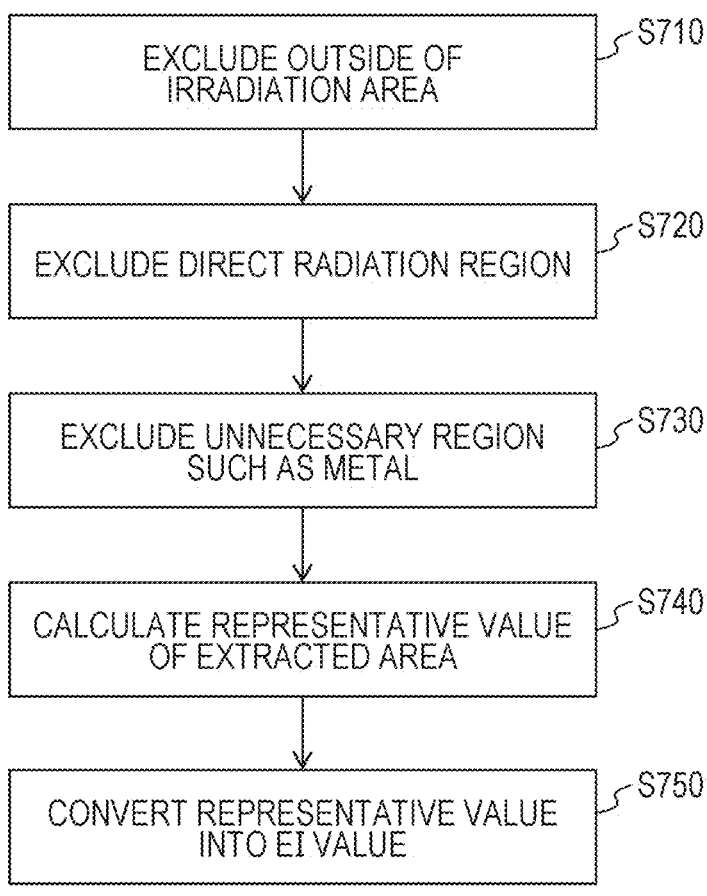
FIG. 7 is a diagram illustrating an example of a flowchart for calculating an EI value.

FIG. 7 illustrates a flowchart in which the dose index generating unit 502 calculates an EI value from an image.

First, in step S710, a region that is obviously outside a region of interest of a diagnostic image, which is not irradiated with X-rays, is excluded from an EI value calculation area in a captured image. Examples of a method to be used include a method of performing calculation based on collimator information or tube-FPD distance (FDD) information, a method of extracting an irradiation region from an image by using imaging area information obtained in advance, and a method of AI determination using machine learning.

Next, in step S720, a direct radiation region is specified, and a region outside the region of interest is excluded from the EI value calculation area. Examples of a method include an empirical fixed threshold method, a mode method, a differential histogram method, a p-tile method, and a discriminant analysis method.

Furthermore, in step S730, a low-dose region which is within the region of interest but is not to be used as a dose index of the region of interest in a normal diagnostic image is excluded from the EI value calculation area. Examples of a method include a region growing method and a snake method. The foregoing processing is applied to the region for calculating a dose index value determined in advance by the dose index region determining unit 501, or to the entire image, and then the region for calculating the dose index value determined by the dose index region determining unit 501 is cut out to determine the region for calculating the EI value. The exclusion of a region outside of an irradiation area, the exclusion of a direct radiation region, and the exclusion of an unnecessary region such as metal may be selectively performed or may not be performed.

Next, in step S740, a representative value such as an average or a median is calculated.

Finally, in step S750, the representative value is converted into an EI value such that 100=1 µGy holds.

At the same time, a deviation DI from EIt is calculated, and the operator determines whether capturing of the X-ray image has been performed with an expected X-ray dosage.

The dose index display unit 503 displays the dose index value generated by the dose index generating unit 502 on the display apparatus 314. The dose index value may be displayed as an annotation at an end portion of a radiographic image as illustrated in FIG. 8A, or may be displayed so as to be superimposed on an image region for which the dose index value is calculated as illustrated in FIG. 8B. Furthermore, the dose index value may be displayed separately from the radiographic image as illustrated in FIG. 8C, or may be displayed without a radiographic image as illustrated in FIG. 8D. Alternatively, as illustrated in FIG. 9A, the dose index value may be displayed on the radiographic image in a gray scale (or a color scale), or as illustrated in FIG. 9B, only the gray scale (or the color scale) may be separately displayed. Of course, a combination may be used as illustrated in FIG. 9C.

FIGS. 8A to 8D and FIGS. 9A to 9C illustrate examples of a method of displaying dose index values by using characters, colors, and so forth. The display method is defined by any combination of identifiable expressions, such as characters, symbols, figures, sizes, colors, and shapes. Furthermore, the dose index display unit 503 may display a target dose index and a deviation index value together with a dose index value. The target dose index and the deviation index may be displayed by the same display method as that for the dose index value, or may be displayed by any different display methods. Instead of displaying the dose index value or the deviation index value, for example, a warning dialog may be displayed when the dose index value or the deviation index value is equal to or larger than a predetermined threshold value. The number of threshold values may be one, or a threshold value may be provided for each region for which the dose index value is calculated.

Figure 10:
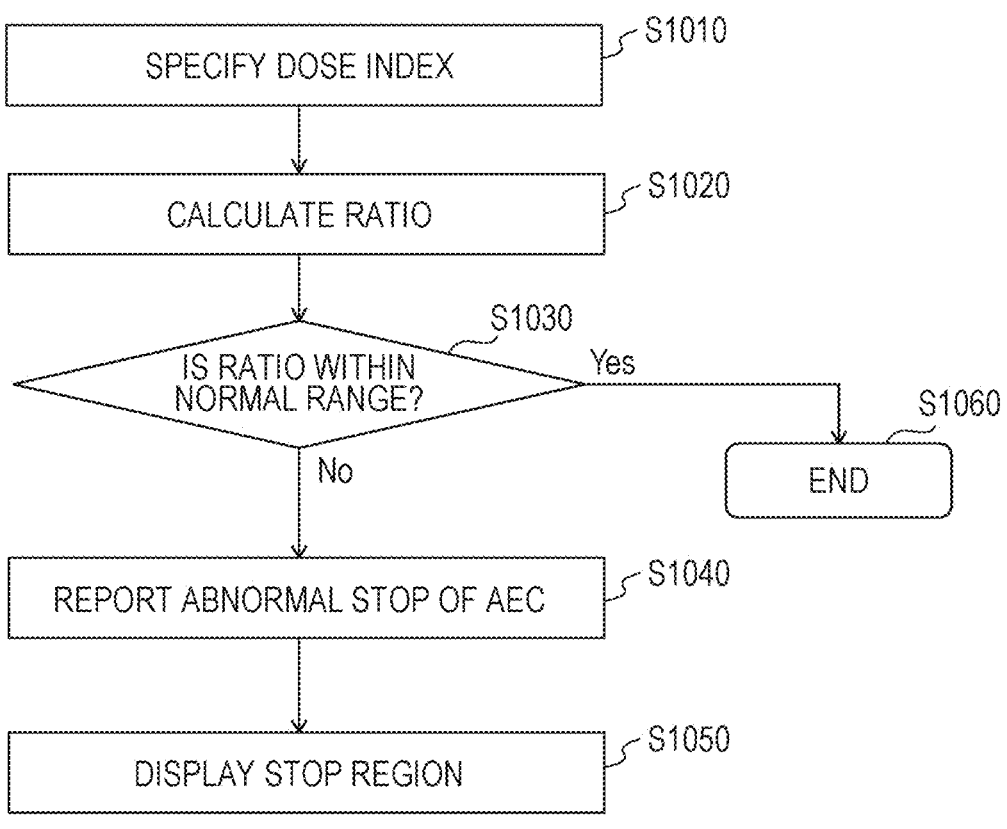
FIG. 10 is a diagram illustrating an example of a flowchart including specifying of a dose index value to displaying of a stop region.

The dose index specifying unit 504, the dose index ratio calculating unit 505, the unexpected stop reporting unit 506, and the stop region display unit 507 will be described with reference to FIG. 10. A description will be given of a procedure of specifying a comparative dose, calculating a ratio to a target dose index, reporting abnormal stop of AEC if the ratio is out of the range of a normal value, and displaying a stop region, performed by these units.

First, in step S1010, the dose index specifying unit 504 specifies a region that has caused an imaging unit to transmit an irradiation stop signal, based on the dose index value generated by the dose index generating unit 502 and a stop condition (AND, OR, or AVG) set in the radiation imaging apparatus 300. If irradiation ends before AEC operates and there is no region that has caused the imaging unit to transmit an irradiation stop signal, specification of a region need not be performed. In the present embodiment, the stop condition is acquired from the header information of a captured image. Alternatively, for example, information may be separately received from the radiation imaging apparatus 300 by communication.

Figure 11:
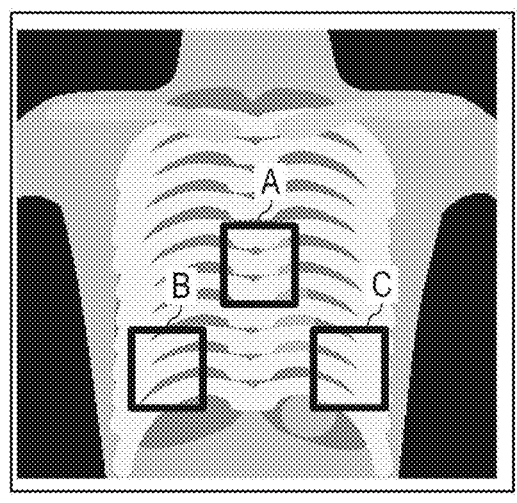
FIG. 11 is a diagram illustrating an example of a method for specifying a dose index value.

As illustrated in FIG. 11, the dose index values of region A, region B, and region C are calculated. In a case where the stop condition is AND, the smallest value among the dose index values of region A, region B, and region C is specified as the dose index value. In a case where the stop condition is OR, the largest value is specified as the dose index value. In a case where the stop condition is AVG, an average value of the dose index values of region A, region B, and region C is specified as the dose index value.

Next, in step S1020, the dose index ratio calculating unit 505 calculates the ratio of the dose index value of the region specified by the dose index specifying unit 504 to the target dose index. Subsequently, whether the calculated ratio is within the range of a normal value, that is, whether the calculated ratio is within an allowable range, is determined. If the calculated ratio is out of the range, the unexpected stop reporting unit 506 reports the determination result. In the present embodiment, a ratio is calculated and whether the ratio is within an allowable range is determined. This means that an allowable range is set for the target dose index value and that whether the dose index value is within the allowable range is determined. That is, determining of whether the relationship between the target dose index value and the dose index value satisfies a setting condition is also included in setting of the allowable range of the target dose index value and determining of whether the dose index value is within the allowable range. Thus, the dose index ratio calculating unit 505 may be regarded as an allowable range setting unit that sets the allowable range of the target dose index value or a determination unit that determines whether the dose index value is within the allowable range. As described above, the dose index ratio calculating unit 505 calculates the ratio of the dose index value of the region specified by the dose index specifying unit 504 to the target dose index, and thus the dose index specifying unit 504 has a part of the function of the determination unit. As described above, the dose index specifying unit 504 has a function of selecting a predetermined region among a plurality of regions based on the stop condition.

If a region is not specified by the dose index specifying unit 504, calculation of a ratio is not performed. In the present embodiment, the target dose index is calculated based on information about a radiation stop target value stored in the header of the captured image, but the present invention is not limited thereto. In the present embodiment, the ratio of the dose index value to the target dose index is calculated, but the calculation method is not limited thereto. For example, a deviation DI may be obtained.

Subsequently, if the ratio calculated by the dose index ratio calculating unit 505 is out of the range of a normal value, the unexpected stop reporting unit 506 makes a report in accordance with the value (S1030, S1040). For example, the contents of the report may be different between a case where the value is above an upper limit threshold value and a case where the value is below a lower limit threshold value. If specification of a region is not performed by the dose index specifying unit 504, a report may be made indicating that irradiation ended before AEC operates. Alternatively, in response to a stop notification not being provided to the radiation generating apparatus 324 by the radiation-generating-apparatus control unit 403, a report may be made indicating that irradiation ended before AEC operates. If the ratio calculated by the dose index ratio calculating unit 505 is within the range of a normal value, the process ends (S1060).

The contents of the report may be different between a case where the communication between the radiation imaging apparatus 300 and the control apparatus 310 is wired communication and a case where the communication therebetween is wireless communication.

Finally, in step S1050, if the ratio calculated by the dose index ratio calculating unit 505 is out of the range of a normal value, the stop region display unit 507 displays the region that has caused the irradiation stop signal to be transmitted. That is, at least one region is selected from among the plurality of regions in accordance with the stop condition. If the dose index value of the selected region is out of the allowable range, the determination result is displayed such that the position of the selected region is recognizable. This will be described with reference to FIG. 12.

Figure 12:
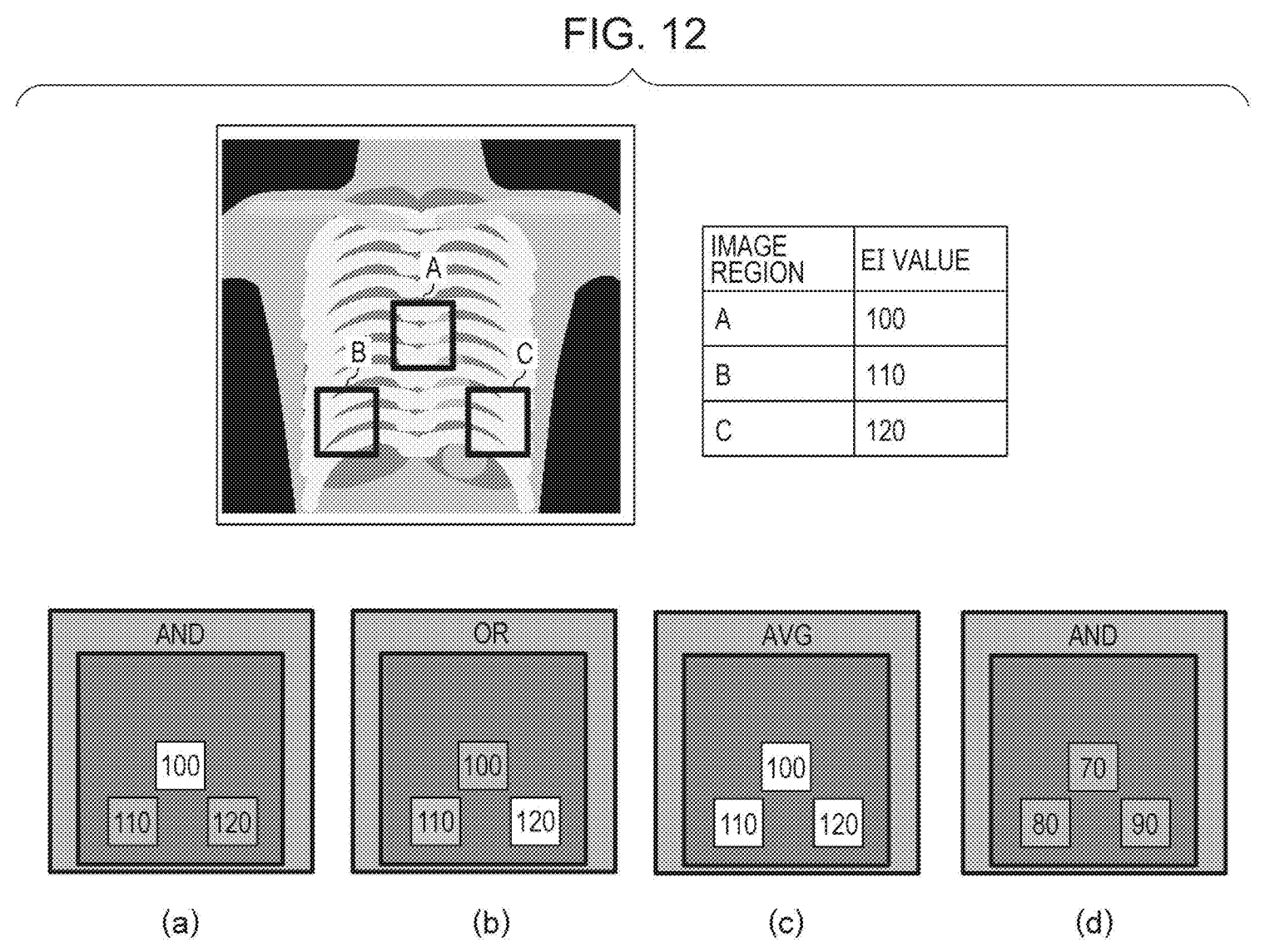

As illustrated in FIG. 12, in the present embodiment, receptor fields and the dose index values of the respective receptor fields are displayed in accordance with the relative positions in the image, and the region that has caused an irradiation stop signal to be transmitted is displayed so as to be distinguished from the other receptor fields. As illustrated in part (a) of FIG. 12, in a case where the stop condition is AND, the region having the smallest dose index value among region A, region B, and region C is displayed in a color different from the colors of the other regions. As illustrated in part (b) of FIG. 12, in a case where the stop condition is OR, the region having the largest dose index value is displayed in a color different from the colors of the other regions. As illustrated in part (c) of FIG. 12, in a case where the stop condition is AVG, region A, region B, and region C are displayed in the same color. In a case where the stop condition is AND, all the regions may be displayed in the same color to clearly indicate that the dose index values of all the regions are larger than or equal to the target dose index value. In a case where the stop condition is AVG, only regions having a dose index value that is larger than or equal to the target dose index value may be displayed in the same color so as to be distinguished from a region having a dose index value that is smaller than the target dose index value. As illustrated in part (d) of FIG. 12, in a case where no region is specified by the dose index specifying unit 504, all the receptor fields may be displayed without being distinguished from each other.

In FIG. 12, the dose index value of each region of interest is indicated by a numerical value, and the stop region is displayed in a color different from the colors of the other regions. However, the display method is not limited thereto, and is defined by any combination of identifiable expressions, such as characters, symbols, figures, sizes, colors, and shapes.

Alternatively, as illustrated in FIG. 13, displayed contents may vary depending on whether the ratio of the region that has caused an irradiation stop signal to be transmitted is below a lower limit threshold value or above an upper limit threshold value. The displayed contents may be expressed by characters as illustrated in part (a) of FIG. 13, or may be expressed using colors as illustrated in part (b) of FIG. 13. In this way, the user is able to know whether X-rays are weaker or stronger than expected only by checking the displayed contents, and is able to use the displayed contents as a foothold for reviewing the environment and setting. In FIG. 13, whether the ratio is above the upper limit threshold value or below the lower limit threshold value is expressed by characters and colors. However, the expression method is not limited thereto, and is defined by any combination of identifiable expressions, such as numerical values, symbols, figures, sizes, colors, and shapes.

Next, an imaging operation of the radiation imaging system 10 will be described with reference to FIG. 14.

Upon the power of the radiation imaging system 10 being turned on and the power of the radiation imaging apparatus 300 being turned on, initial settings are made and communication with the control apparatus 310 is enabled.

In step S101, the radiation imaging system 10 sets subject information, such as the ID, the name, and the date of birth of the subject 306, in the control apparatus 310. In step S102, the radiation imaging system 10 sets imaging information, such as the imaging area of the subject 306, a receptor field, and a target dose index. The subject information and the imaging information may be automatically set by selecting an examination order received via the in-hospital LAN 315, for example. The imaging information may be set by selecting a preset imaging protocol.

At this time, the operator 312 may directly input and set the information of the subject 306 and the imaging information.

The radiation imaging system 10 sets a receptor field of the radiation imaging apparatus 300, based on the input information. The operator 312 fixes the posture of the subject 306 and the radiation imaging apparatus 300 after the information of the subject 306 and the information of the imaging area have been set in the control apparatus 310. Furthermore, the operator 312 inputs, to the control apparatus 310, a dose, a maximum irradiation time, a tube current, a tube voltage, area information, a receptor field, a target dose index, and so forth. The control apparatus 310 transmits, to the radiation imaging apparatus 300 and the radiation generating apparatus 324, the radiation irradiation condition, the area information, the receptor field, the target dose index, and so forth that have been input. In the system, the information may be input to the radiation generating apparatus 324, and the information may be provided to the control apparatus 310 and the radiation imaging apparatus 300.

After preparation for imaging has been completed, the operator 312 presses the radiation irradiation switch 311 in step S103. Upon the radiation irradiation switch 311 being pressed, radiation is emitted from the radiation source 325 toward the subject 306. At this time, the radiation imaging apparatus 300 communicates with the radiation generating apparatus 324 to control the start of radiation irradiation. The radiation applied to the subject 306 is transmitted through the subject 306 and enters the radiation imaging apparatus 300. In a case where setting has been done to use the reached dose monitoring function, the radiation imaging apparatus 300 detects, with the detection pixels 101, radiation that has entered the receptor field, and calculates, with the signal processing unit 224, an integrated amount of irradiation which is an integrated value of a dose (reached dose) detected in a predetermined period. The imaging-apparatus control unit 225 calculates a reference threshold value from the information on the integrated amount of irradiation received from the signal processing unit 224, the area information and imaging condition input by the operator 312, and so forth, and determines the radiation irradiation stop timing in accordance with the mode set in the radiation-generating-apparatus control unit 403. In accordance with the determined radiation irradiation stop timing, the radiation imaging apparatus 300 provides a stop notification to the radiation generating apparatus 324 via the radiation-imaging-apparatus communication cable 307, the communication control apparatus 323, and the radiation-generating-apparatus communication cable 327. In accordance with the notified radiation irradiation stop timing, the radiation generating apparatus 324 stops radiation irradiation. The radiation imaging apparatus 300 provides the notification to stop radiation irradiation as a result of detecting radiation, but the present invention is not limited thereto. The radiation imaging apparatus 300 may transmit a reached dose at a predetermined time interval as a detection result, and the radiation generating apparatus 324 may calculate an integrated value of the reached dose. After the radiation irradiation has stopped, the radiation imaging apparatus 300 converts the incident radiation into visible light, and then detects the visible light as a radiographic image signal by the photoelectric conversion element. The radiation imaging apparatus 300 drives the photoelectric conversion element to read out the radiographic image signal, and converts the analog signal into a digital signal by an AD conversion circuit to obtain digital radiographic image data.

In step S104, the obtained digital radiographic image data is transferred from the radiation imaging apparatus 300 to the control apparatus 310 via the radiation-imaging-apparatus communication cable 307, the communication control apparatus 323, and the radiation-room communication cable 316. The control apparatus 310 performs image processing on the received digital radiographic image data. The control apparatus 310 causes the display apparatus 314 to display a radiographic image based on the radiographic image data subjected to the image processing. The control apparatus 310 also functions as an image processing apparatus and a display control apparatus.

In step S105, receptor fields are determined as calculation regions.

In step S106, the control apparatus 310 transfers the received digital radiographic image data to the dose index generating unit 502. By using the received radiographic image data, the dose index generating unit 502 calculates dose index values of the determined calculation regions, and then calculates deviation index values in step S107. In the present embodiment, the dose index values and the deviation index values are calculated by the control apparatus 310. However, the calculation may be performed by the radiation imaging apparatus 300 or another component.

Figures 15A, 15B, 15C:
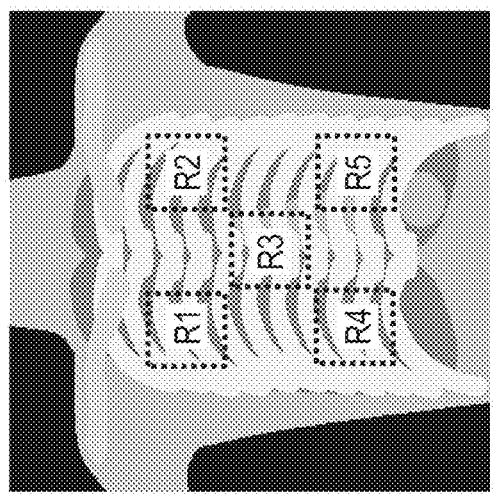
FIGS. 15A to 15C are diagrams illustrating an example of a method for displaying dose index values.

In step S108, the dose index values and the deviation index values calculated by the dose index generating unit 502 are transferred to the dose index display unit 503, and are displayed in the manner illustrated in FIGS. 15A to 15C, for example. Referring to FIGS. 15A to 15C, imaging is performed on a lung-field region in which the reached dose monitoring function is enabled. The imaging is performed, with both lung regions R1 and R2 illustrated in FIG. 15B being receptor fields. As illustrated in FIGS. 15A and 15C, as a result of displaying the dose index values and the deviation index values for the individual regions, it is possible to determine whether the dose for the receptor field set as a region of interest is appropriate. The region of interest is not limited to the receptor field of the reached dose monitoring function, and any region may be set, or the operator 312 may change the region of interest after imaging. The setting as to whether display on the display apparatus 314 is to be performed may be made before imaging or may be made by the operator 312 after imaging. The display setting may be changed by the setting of the reached dose monitoring function. Alternatively, if a received dose index value or deviation index value satisfies a specific condition, control may be performed to display an icon or dialog (not illustrated). The specific condition may be, for example, a case where the dose index value or the deviation index value is larger than a predetermined value.

In step S109, a region that has caused the radiation imaging apparatus 300 to transmit an irradiation stop signal is specified, based on the dose index values calculated by the dose index generating unit 502 and the stop condition (AND, OR, or AVG) set in the radiation imaging apparatus 300. The stop condition is acquired from the header information of the captured image, but is not limited thereto. At this time, if irradiation ends before AEC operates and there is no region that has caused the imaging unit to transmit an irradiation stop signal, specification of a region need not be performed.

In step S110, the ratio of the dose index value specified in step S109 to the target dose index value is calculated. If the ratio is out of the range of a normal value, a report is made in step S111, and the region that has caused the irradiation stop signal to be transmitted is displayed in step S112. If no region is specified in step S109, step S110 is skipped, and a report is made in step S111.

As a result of constructing the above-described system, if AEC is not stopped at a normal timing in AEC imaging, the operator 312 is able to immediately notice an environmental deficiency or a setting error by checking the contents of a report and a displayed region.

For example, if more X-rays than expected are detected in a wireless communication environment and if a report for prompting the operator 312 to check the communication state is made, the operator 312 is able to notice that imaging is being performed under an environment of unstable wireless communication. In addition, if less X-rays than expected are detected and if a report for prompting the operator 312 to determine whether an X-ray tube is appropriately positioned is made, the operator 312 is able to determine the positioning of the X-ray tube and the region that has caused an irradiation stop signal to be transmitted. As a result, the operator 312 is able to notice that the positioning of the X-ray tube is inappropriate. In addition, as a result of reporting that irradiation ended before AEC operates, the user is able to notice that he/she released the radiation irradiation switch early.

The embodiment can also be implemented by a computer or a control computer executing a program (computer program). In addition, means for supplying the program to the computer, for example, a computer-readable recording medium such as a CD-ROM storing the program, or a transmission medium such as the Internet for transmitting the program, is also applicable as an embodiment. The above-described program is also applicable as an embodiment. The above-described program, recording medium, transmission medium, and program product are included in the scope of the present invention.

The embodiment has been described in detail. The present invention is not limited to a specific embodiment, for example, the present invention is applicable to not only capturing of a still image but also capturing of a moving image. Various modes within the range not departing from the gist of the present invention are also included in the scope of the present invention. Furthermore, the above-described embodiment is merely one embodiment, and inventions easily imaginable from the above-described embodiment are also included in the scope of the present invention.

According to one or more embodiments of the present invention, it is possible to determine whether AEC is operating correctly.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2022-172096, 2022-172097, and 2022-172095, filed Oct. 27, 2022, which are hereby incorporated by reference herein in their entirety.

What is claimed is:

1. A radiation imaging system comprising:
a radiation imaging apparatus including
a conversion unit configured to generate electric charge in response to irradiation with radiation, and
a transmission unit configured to transmit, based on the electric charge generated by the conversion unit and a target value, a signal related to control of irradiation with radiation to an external apparatus; and
a control apparatus including
a dose index generating unit configured to generate a target dose index value that is based on the target value, and a dose index value that is based on information regarding electric charge, the information being acquired from the radiation imaging apparatus,
an allowable range setting unit configured to set an allowable range of the target dose index value, and
a determination unit configured to determine whether the dose index value is within the allowable range.

2. The radiation imaging system according to claim 1, wherein the allowable range setting unit is configured to set the allowable range, based on a ratio of the dose index value to the target dose index value.

3. The radiation imaging system according to claim 2, wherein the control apparatus further includes a reporting unit configured to, in a case where a determination result of the determination unit indicates that the dose index value is out of the allowable range, report the determination result.

4. The radiation imaging system according to claim 3, wherein the reporting unit includes a display unit.

5. The radiation imaging system according to claim 3, wherein contents of a report made by the reporting unit are different between a case where the determination result of the determination unit indicates that the dose index value is above an upper limit of the allowable range and a case where the determination result of the determination unit indicates that the dose index value is below a lower limit of the allowable range.

6. The radiation imaging system according to claim 3, wherein
the radiation imaging apparatus is capable of transmitting the signal related to control of irradiation with radiation to the external apparatus by wired communication or wireless communication, and
contents of a report made by the reporting unit are different between a case where the signal is transmitted by wired communication and a case where the signal is transmitted by wireless communication.

7. The radiation imaging system according to claim 3, wherein
the transmission unit is capable of notifying the control apparatus of whether the signal related to control of irradiation with radiation has been transmitted to the external apparatus, and
contents of a report made by the reporting unit are different between a case where the transmission unit has transmitted the signal to the external apparatus and a case where the transmission unit has not transmitted the signal to the external apparatus.

8. A radiation imaging system comprising:
a radiation imaging apparatus including
a conversion unit configured to generate electric charge in response to irradiation with radiation, and
a transmission unit configured to transmit, based on the electric charge generated by the conversion unit and a target value, a signal related to control of irradiation with radiation to an external apparatus; and
a control apparatus including
a dose index generating unit configured to generate a target dose index value that is based on the target value, and a dose index value that is based on information regarding electric charge, the information being acquired from the radiation imaging apparatus,
an allowable range setting unit configured to set an allowable range of the target dose index value, and
a determination unit configured to determine whether the dose index value is within the allowable range, wherein
the conversion unit includes a plurality of regions,
the signal transmitted by the transmission unit is a signal for providing an instruction to stop irradiation with radiation, the signal being transmitted based on electric charge of each of the plurality of regions, the target value, and a stop condition,
the dose index generating unit is configured to generate a dose index value for each of the plurality of regions of the conversion unit, and
the determination unit is configured to, in a case where the stop condition is AND, determine whether a smallest dose index value among the dose index values of the plurality of regions is within the allowable range.

9. The radiation imaging system according to claim 8, wherein the allowable range setting unit is configured to set the allowable range, based on a ratio of the dose index value to the target dose index value.

10. A radiation imaging system comprising:
a radiation imaging apparatus including
a conversion unit configured to generate electric charge in response to irradiation with radiation, and
a transmission unit configured to transmit, based on the electric charge generated by the conversion unit and a target value, a signal related to control of irradiation with radiation to an external apparatus; and
a control apparatus including
a dose index generating unit configured to generate a target dose index value that is based on the target value, and a dose index value that is based on information regarding electric charge, the information being acquired from the radiation imaging apparatus,
an allowable range setting unit configured to set an allowable range of the target dose index value, and a determination unit configured to determine whether the dose index value is within the allowable range, wherein the conversion unit includes a plurality of regions, the signal transmitted by the transmission unit is a signal for providing an instruction to stop irradiation with radiation, the signal being transmitted based on electric charge of each of the plurality of regions, the target value, and a stop condition, the dose index generating unit is configured to generate a dose index value for each of the plurality of regions of the conversion unit, and the determination unit is configured to, in a case where the stop condition is OR, determine whether a largest dose index value among the dose index values of the plurality of regions is within the allowable range.

11. A radiation imaging system comprising:

a radiation imaging apparatus including a conversion unit configured to generate electric charge in response to irradiation with radiation, and a transmission unit configured to transmit, based on the electric charge generated by the conversion unit and a target value, a signal related to control of irradiation with radiation to an external apparatus; and a control apparatus including a dose index generating unit configured to generate a target dose index value that is based on the target value, and a dose index value that is based on information regarding electric charge, the information being acquired from the radiation imaging apparatus, an allowable range setting unit configured to set an allowable range of the target dose index value, and a determination unit configured to determine whether the dose index value is within the allowable range, wherein the conversion unit includes a plurality of regions, the signal transmitted by the transmission unit is a signal for providing an instruction to stop irradiation with radiation, the signal being transmitted based on electric charge of each of the plurality of regions, the target value, and a stop condition, the dose index generating unit is configured to generate a dose index value for each of the plurality of regions of the conversion unit, and the determination unit is configured to, in a case where the stop condition is AVG, determine whether an average value of the dose index values of the plurality of regions is within the allowable range.

12. A radiation imaging system comprising:

a radiation imaging apparatus including a conversion unit configured to generate electric charge in response to irradiation with radiation, and a transmission unit configured to transmit, based on the electric charge generated by the conversion unit and a target value, a signal related to control of irradiation with radiation to an external apparatus; and a control apparatus including a dose index generating unit configured to generate a target dose index value that is based on the target value, and a dose index value that is based on information regarding electric charge, the information being acquired from the radiation imaging apparatus, an allowable range setting unit configured to set an allowable range of the target dose index value, a determination unit configured to determine whether the dose index value is within the allowable range, and a display unit configured to display a determination result, wherein the conversion unit includes a plurality of regions, the signal transmitted by the transmission unit is a signal for providing an instruction to stop irradiation with radiation, the signal being transmitted based on electric charge of each of the plurality of regions, the target value, and a stop condition, the dose index generating unit is configured to generate a dose index value for each of the plurality of regions of the conversion unit, the determination unit is configured to, based on the stop condition, select at least one region among the plurality of regions and make a determination of whether the dose index value of the selected region is within the allowable range, and the display unit is configured to, in a case where a determination result of the determination indicates that the dose index value of the selected region is out of the allowable range, display the determination result such that a position of the selected region is recognizable.

13. The radiation imaging system according to claim 12, wherein the allowable range setting unit is configured to set the allowable range, based on a ratio of the dose index value to the target dose index value.

14. The radiation imaging system according to claim 13, wherein the display unit is configured to display the determination result in accordance with magnitude of the ratio of the determination result.

15. A radiation imaging system comprising:

a radiation imaging apparatus including a conversion unit configured to generate electric charge in response to irradiation with radiation, and a transmission unit configured to transmit, based on the electric charge generated by the conversion unit and a target value, a signal related to control of irradiation with radiation to an external apparatus; and a control apparatus including a dose index generating unit configured to generate a target dose index value that is based on the target value, and a dose index value that is based on information regarding electric charge, the information being acquired from the radiation imaging apparatus, an allowable range setting unit configured to set an allowable range of the target dose index value, a determination unit configured to determine whether the dose index value is within the allowable range, and a reporting unit configured to report a determination result of the determination unit or whether irradiation with radiation is ended before automatic exposure control operates.

16. The radiation imaging system according to claim 15, wherein the allowable range setting unit is configured to set the allowable range, based on a ratio of the dose index value to the target dose index value.

17. The radiation imaging system according to claim 16, wherein the reporting unit reports the determination result in a case where the determination result of the determination unit indicates that the dose index value is out of the allowable range.

18. The radiation imaging system according to claim 17, wherein the reporting unit includes a display unit.

19. The radiation imaging system according to claim 17, wherein contents of a report made by the reporting unit are different between a case where the determination result of the determination unit indicates that the dose index value is above an upper limit of the allowable range and a case where the determination result of the determination unit indicates that the dose index value is below a lower limit of the allowable range.

20. The radiation imaging system according to claim 17, wherein the radiation imaging apparatus is capable of transmitting the signal related to control of irradiation with radiation to the external apparatus by wired communication or wireless communication, and contents of a report made by the reporting unit are different between a case where the signal is transmitted by wired communication and a case where the signal is transmitted by wireless communication.

21. The radiation imaging system according to claim 17, wherein the transmission unit is capable of notifying the control apparatus of whether the signal related to control of irradiation with radiation has been transmitted to the external apparatus, and contents of a report made by the reporting unit are different between a case where the transmission unit has transmitted the signal to the external apparatus and a case where the transmission unit has not transmitted the signal to the external apparatus.

22. A radiation imaging system comprising:

a radiation imaging apparatus including a conversion unit configured to generate electric charge in response to irradiation with radiation, and a transmission unit configured to transmit, based on the electric charge generated by the conversion unit and a target value, a signal related to control of irradiation with radiation to an external apparatus; and a control apparatus including a dose index generating unit configured to generate a target dose index value that is based on the target value, and a dose index value that is based on information regarding electric charge, the information being acquired from the radiation imaging apparatus, an allowable range setting unit configured to set an allowable range of the target dose index value, a determination unit configured to determine whether the dose index value is within the allowable range, and a display unit configured to display a determination result, wherein the conversion unit includes a plurality of regions, the signal transmitted by the transmission unit is a signal for providing an instruction to stop irradiation with radiation, the signal being transmitted based on electric charge of each of the plurality of regions, the target value, and a stop condition, the dose index generating unit is configured to generate a dose index value for each of the plurality of regions of the conversion unit, the determination unit is configured to, based on the stop condition, select at least one region among the plurality of regions and make a determination of whether the dose index value of the selected region is within the allowable range, and the display unit is configured to, in a case where a determination result of the determination indicates that the dose index value of the selected region is out of the allowable range, display the determination result such that a position of the selected region is recognizable or display whether irradiation with radiation is ended before automatic exposure control operates.

* * * * *